United States Patent [19]

Neeley et al.

[11] 3,961,898

[45] June 8, 1976

[54] COMPARATOR CIRCUIT FOR AUTOMATIC ANALYSIS APPARATUS

[75] Inventors: William E. Neeley, Rockville, Md.; Stephen C. Wardlaw, Branford, Conn.; Maurice E. T. Swinnen, Lanham, Md.

[73] Assignee: The United States of America as represented by the Secretary of the Army, Washington, D.C.

[22] Filed: Jan. 14, 1975

[21] Appl. No.: 541,033

[52] U.S. Cl............................. 23/253 R; 356/181; 356/204; 356/229; 346/33 A; 235/151.35
[51] Int. Cl.²......................................... G01N 21/26
[58] Field of Search............. 23/230 R, 259, 253 R; 356/181, 204, 229; 346/33 A; 235/151.35

[56] References Cited
UNITED STATES PATENTS

| 3,480,369 | 11/1969 | Smythe et al. | 23/230 R |
| 3,784,310 | 1/1974 | Barton et al. | 23/253 R |
| 3,804,593 | 4/1974 | Smythe | 23/253 X |

*Primary Examiner*—R.E. Serwin
*Attorney, Agent, or Firm*—William G. Gapcynski; Lawrence A. Neureither; Frank R. Agovino

[57] ABSTRACT

The invention concerns an automatic continuous-flow fluid analyzer of the type wherein a stream of fluid, segmented by air bubbles or other separating medium inert to the fluid to be analyzed, passes through a colorimeter flow cell. The bubble artifact is eliminated from the photoconductor signal while allowing the signal produced from the fluid segment to remain intact. This is accomplished by means of a signal comparator which operates as a digitally controlled differentiator, but could alternatively be a purely analog differentiator. The signal comparator through continual signal comparisons momentarily samples and stores a photoconductor output.

For a finite period of time, the stored value is compared with all subsequent succeeding photoconductor output signals. If any signal that follows varies outside a preset range from the stored value, the comparator logic concludes that an air bubble is passing and the output to the recorder is not changed. The recorder continues to record from the signal in the memory means at all times. If the signal that follows remains constant as compared to the stored value, the comparator logic concludes that a fluid segment is in the flow cell and the signal at that time is transferred to the memory means and to the recorder.

5 Claims, 6 Drawing Figures

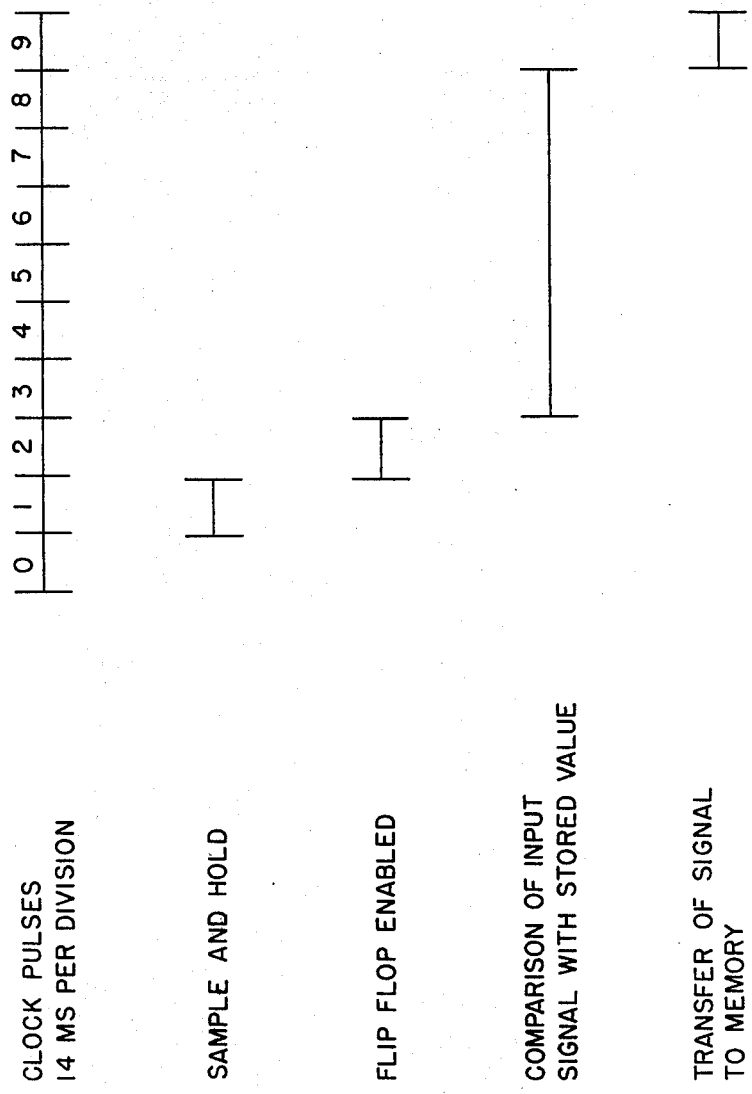

COMPARATOR CIRCUIT FOR AUTOMATIC ANALYSIS APPARATUS

The invention described herein may be manufactured and used by or for the Government for governmental purposes without payment of any royalty thereon.

BACKGROUND OF THE INVENTION

1. Field of the Invention

The invention is in the field of test apparatus employing a colorimeter flow cell for determining the quantitative analysis of bubble separated segments of fluids. Fluids as herein used refer both to liquids and gases.

2. Description of the Prior Art

In U.S. Pat. No. 3,804,593 by William J. Smythe et al, an apparatus and method is described wherein an automatic analysis apparatus includes an indexible table supporting a plurality of liquid sample containers, a stationary reagent liquid container, two off-take tubes, one tube insertable in a presented thereto sample container, the other tube insertable in the reagent container, means for concurrently inserting both tubes repeatedly into their respective containers to provide a flowing stream of segments of liquid sample interspersed by air segments, and a smilar stream of segments of reagent. These streams are merged to form a stream of liquid and air segments, which stream of liquid and air segments is passed through the sight passageway of a flow cell of a colorimeter. A recorder is coupled to the detector side of the colorimeter through an electrical switch which interrupts the operation of said recorder whenever the sample reagent segment volume is not equal to the volume of the sight passageway of the flow cell, thereby shutting down the recorder for some period of time in order to allow the air segment to completely clear the sight passageway of the flow cell.

In allowing the segments to remain intact within the sight passage of the flow cell, system efficiency is significantly increased; however, this advantage is practically deficient when the recorder must be shut down by a switching means in order to allow the sight passage of the flow cell to become completely clear of air segments. If the recorder were allowed to continue in operation during the progression of an air segment through the sight passage of the flow cell, the readout of the recording would show corresponding spikes or non essential data which clutters the desired sample curve data. Another advantage of the present invention over the prior art is in that irregularly spaced air bubbles can be used with the comparator but, the fluid segment volume must be at least equal to the volume of the sight passageway of the flow cell.

R. L. Habig et al in Clinical Chemistry 15, 1045 (1969) and W. H. Walker et al in Clin. Chim. Acta 27, 421 (1970) taught removing the air bubble or debubbling the segmented fluid sample to be tested at a point just prior to entry into the sight passage of the flow cell. Habig et al also taught elimination of the need for a debubbler by utilizing a bubble gating flow cell. Their device monitored flow cell conductance and deactivated the system output when bubbles passed through the photometer flow cell. This latter technique, although useful for testing, would not withstand daily technician use and abuse. The herein described invention overcomes the deficiencies of the conductance gate. In the case of utilizing a debubbler the recorder is allowed to operate continuously, but the test results are less efficient because of the dispersion of the sample.

SUMMARY OF THE INVENTION

The present invention concerns an improvement in a continuous-flow fluid analyzer employing a colorimeter flow cell for determining the quantitative analysis of bubble separated segments of fluid. The improvement concerns a signal comparator comprising a means to momentarily sample and store the output signal from a photodetector, a means to continually comparator the stored value with all subsequent succeeding photodetector outputs for a finite period of time, a means to logically conclude that an air bubble is passing through the sight passage of the flow meter, and a means to logically instruct the recorder to maintain its last acceptable output until a new output is accepted. The bubble artifact is completely removed by the signal compartor while producing a precise and reliable result and while allowing the absorbance of the individual fluid segment to pass without interruption of the recorder's operation. The apparatus is inexpensive, easy to use, and does not require any adjustment by a technician.

The instant invention avoids the need for removing the air bubble separating segments of fluid to be tested in apparatus employing a colorimeter flow cell or deactivating the light source for the colorimeter flow cell while the air bubble is passing through the cell.

It is accordingly a primary object of the invention to eliminate recording the bubble artifact from the photoconductor signal in a continuous-flow fluid analyzer having a colorimeter flow cell while allowing the signal produced by the fluid segment to remain intact and without interruption of the recorder's operation.

It is a further object of the instant invention to provide in a continuous-flow fluid analyzer having a colorimeter flow cell a signal comparator which samples and stores the photoconductor output and selectively determining signals to be recorded.

It is a further object of the instant invention to provide a signal comparator in a continuous-flow fluid analyzer having a colorimeter flow cell which will permit recording signal outputs from desired segments of segmented fluids.

It is a further object of the instant invention to provide a signal comparator in a continuous-flow fluid analyzer having a colorimeter flow cell to permit use of irregularly spaced bubbles while obtaining a desired photoconductor output with the fluid segments being at least equal to the sight passageway of the flow cell.

It is a further object of the invention to provide a signal comparator in a continuous-flow fluid analyzer of segmented samples wherein said signal comparator operates as a digitally controlled differentiator to eliminate the bubble artifact from the photoconductor signal while allowing the signal produced from the segment to remain intact.

These and other objects will become apparent from the following description wherein:

FIG. 5 illustrates the timing sequence of events.

DESCRIPTION OF THE PREFERRED EMBODIMENT

Figure 1:
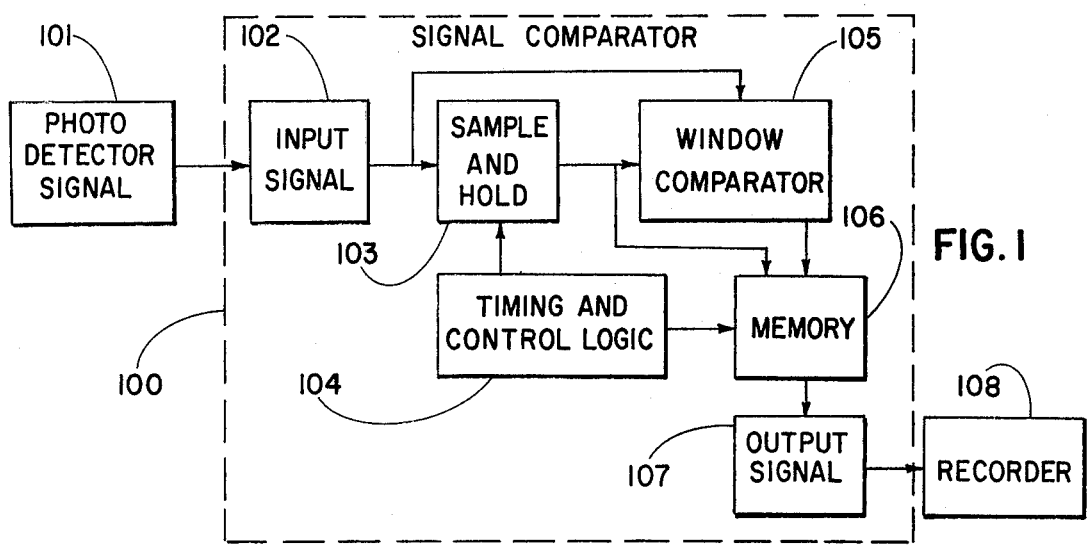
FIG. 1 is a simplified block diagram illustrating the basic design of the signal comparator.
Figure 2:
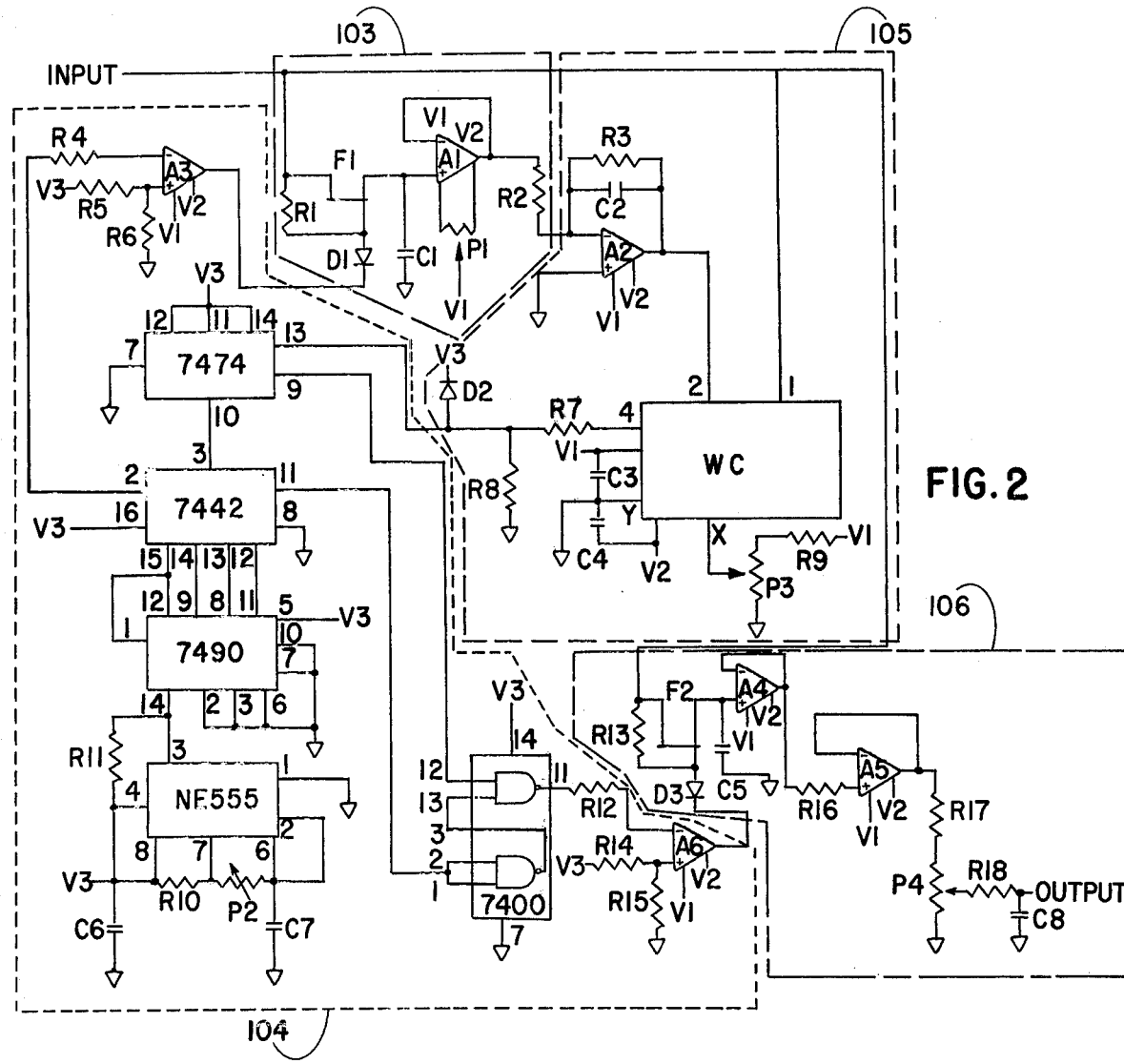
FIG. 2 is the circuit diagram for the block diagram of FIG. 1.

A preferred embodiment of the invention is shown in FIGS. 1 and 2. FIG. 1 is a block diagram of the signal comparator 100 at its proper location in reference to a continuous-flow automatic analyzer. FIG. 2 is a circuit diagram of the signal comparator 100 where all resistors are 1/4 W and all trim pots are 10-turns. The clock pulse interval on NE555 is set at 14ms by adjustment of P2. The final output may be adjusted from 1-60 mV by P4. The following values are for the remainder of the circuit in FIG. 2:

| | | |
|---|---|---|
| A1,4-740 op. amp. | C6- .02 MFd disc | R10- 5.7 kΩ |
| A2,3,5,6- 741 op. amp. | C7- .47 MFd disc | R17- 150 kΩ |
| V1- +15 V dc | C8- 200 MFd, 3V dc | R18- 3.9 kΩ |
| V2- −15 V dc | F1,2-NF510, (FET) | P1- 10 KΩ trim pot |
| V3- +5 V dc | R1,13- 1 MΩ | P2- 1 MΩ trim pot |
| D1,2,3- 1N625 | R2,3,11,16- 1 kΩ | P3- 50Ω trim pot |
| C1- .22 MFd, 15 V dc,Mylar | R4,6,12,15- 10 kΩ | P4- 1 KΩ trim pot |
| C2- .002 MFd disc | R5,14- 16 kΩ | WC-4022/25 Window Comparator; Burr-Brown, Tuscon, Ariz. 85706 |
| C3,4- .1 MFd disc | R7,8- 470Ω | 7474-flip-flop |
| C5- 1 MFd, 15 V dc, Mylar | R9- 20 kΩ | 7442-BCD-to-Decimal Decoder |
| | | 7490-Decade Counter |
| | | NE555-Timer |

FIG. 5 is an example of the timing sequence of events. In FIG. 1, when an output signal is generated from the photodetector 101 of the colorimeter, it becomes the input signal 102 to the signal comparator 100 and is sampled and held in block 103 on clock pulse 1, FIG. 5. On pulse 2, a flip-flop 7474 in the logic block 104 is preset or enabled. On pulses 3–8 the analog input 102 is compared with the previous sampled and held voltage. If the analog input 102 varies above or below the sampled and held voltage by more than 35 mU, the window comparator 105 disables the flip-flop 7474 in the control logic block 104 and no signal transfer occurs on pulse 9 to the memory. The previous value in memory 106 remains unchanged. If none of the subsequent signals vary more than 35 mV from the stored value during pulses 3–8, the window comparator 105 does not disable the flip-flop 7474 in the control logic block 104 and the signal is transferred on pulse 9 to the memory. In this latter case the signal is transferred to the memory 106 for output to the recorder 108. The entire cycle is repeated every 140 ms with a pulse occurring every 14 ms.

Basically, the device operates as a digitally controlled differentiator. When dv/dt>K (where dv is the change in the incoming voltage (absolute value), dt is the time period (84 ms) and K is the window width (35 mV)), the memory is updated for that particular time segment. This operation could also be performed by a purely analog differentiator, but the flexibility and ease of operation would not be as great.

The signal comparator may be used with most continuous-flow analyzers. The comparator operates as a unity gain device (output voltage equals input voltage) and handles 0–10 volt dc signals. If it is used with instruments providing substantially less output voltage, some form of preamplification must be provided; the output signal 107 from the comparator may easily be reduced by means of a simple resistive voltage divider, i.e., FIG. 2, R17 and P4, to fit the recorder's requirements. The bubble pattern is not critical, but as with all continuous-flow systems, the pattern should be uniform for optimum efficiency. The bubble spacing should be such that at least two gating cycles occur for each fluid segment.

Figure 3:
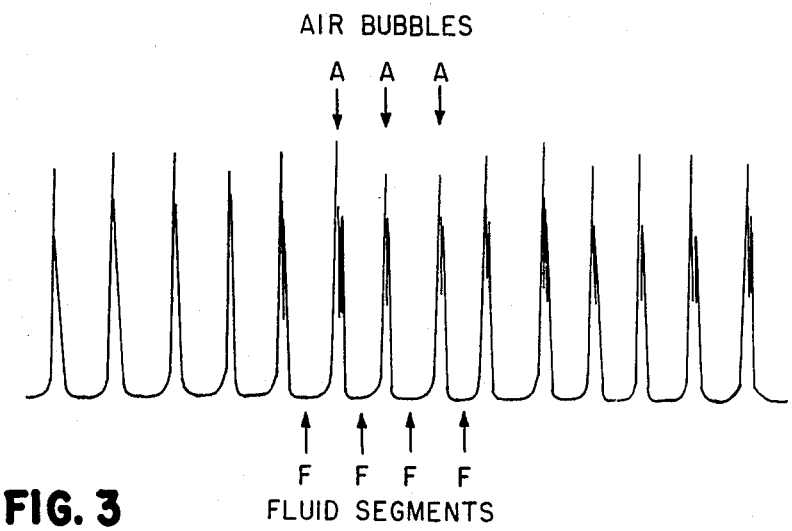
FIG. 3 is the photodetector signal output record as the bubbled stream passes through the sight passsageway of a flow cell of a colorimeter where the signal comparator is not used.
Figure 4:
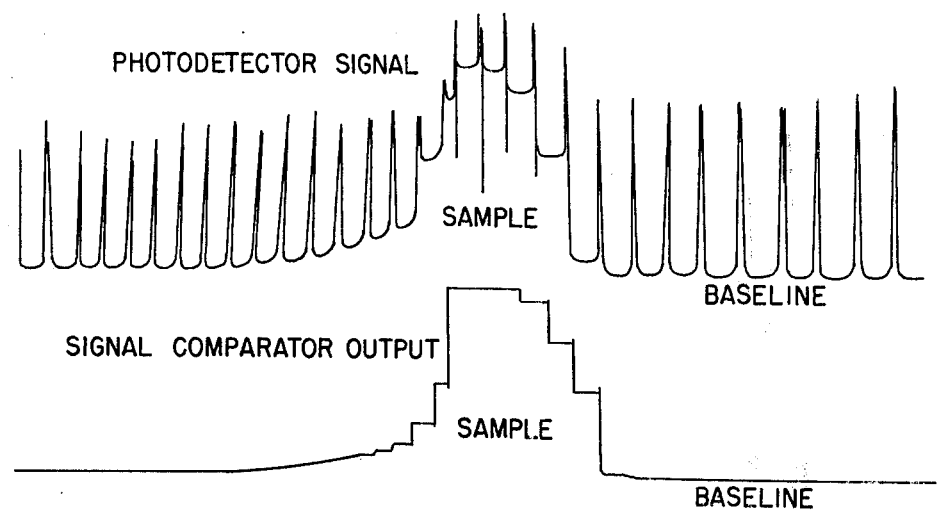
FIG. 4 is the simultaneous recordings of the photodetector signal before and after processing by the signal comparator.

When the signal comparator 100 is not used and the air bubbles are allowed to stream through the photometer flow cell, the recorder readout will have a pattern as shown in FIG. 3. FIG. 4 shows two simultaneous recordings of the photodetector before and after processing by the signal comparator 100.

Figure 6:
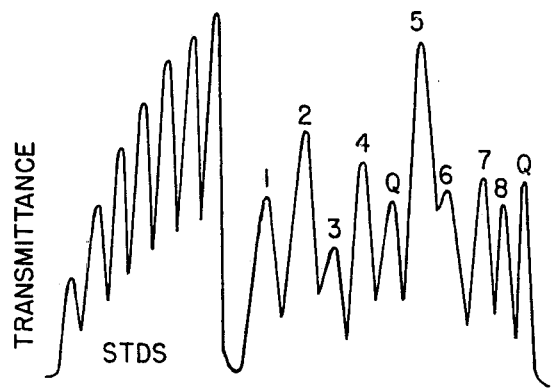
FIG. 6 is the miniaturized continuous-flow analysis for serum glucose at 150 samples/hour, with the use of the signal comparator.

FIG. 6 demonstrates the system efficiency obtained when the signal comparator is used with a miniaturized glucose oxidase method. The first seven peaks are glucose standards ranging from 50–350 mg/dl in 50 mg/dl increments. The following peaks, 1–4 and 5–8, are separate serum samples, followed by quality-control samples (Q). A low-pass filter is used on the output to smooth the peaks, FIG. 2, R18 and C8. The sampling rate is 150 samples per hour with a 3:1 sample-to-wash ratio. The sample volume is 18μl, the reagent consumption is 128μl/sample. Analyses are performed at 99–100% of steady state.

Although a particular embodiment and form of this invention has been illustrated, it is obvious to those skilled in the art that modifications may be made without departing from the scope and spirit of the foregoing disclosure.

We claim:

1. In a continuous-flow fluid analyzer having a colorimeter flow cell and means for conducting fluid segmented by a substance inert to the fluid through the colorimeter flow cell, the improvement comprising:
  a. sampling and storing circuit means receiving signals from the flow cell;
  b. memory and recording means connected to and receiving signals from said sampling and storing means;
  c. differentiator circuit means connected to said sampling and storing means and to said memory and recording means for limiting voltages received by said memory and recording means;
  d. logic circuit means including interconnected repetitive pulse generating means, counter means, decoder means and flip-flop circuit means connected to said sampling and storing circuit means and said memory and recording circuit means, said differentiating circuit means selectively controlling said flip-flop circuit means, whereby a selected output signal from said colorimeter flow cell is stored in said storing circuit means and compared with succeeding signals from said flow cell during a cycle of repetitive pulses, said flow cell output signals conducted to said memory and recording circuit means selectively when the voltage difference of said succeeding and stored pulses does not exceed limiting voltages set by said differentiator circuit means and said flip-flop circuit means is activated to permit recording of said selected flow cell output signals.

2. A digitally controlled signal comparator for use in combination with a continuous-flow fluid analyzer having a colorimeter flow cell with a photodetector and means for conducting fluid segmented by a substance inert to the fluid through the colorimeter flow cell, said signal comparator including interconnected means for sampling and storing the output signal of the photodetector, differentiator circuit means for limiting voltages of output signals from said photodetector to be recorded, a repetitive pulse generator means, a decade counter, a BCD-to-decimal decoder, memory and recording means for the output of said signal comparator, and a flip-flop circuit means whereby without interruption to said recording means an input signal is selected from the output of said photodetector, stored by said storing means for a period determined by the cycle of said decade counter, pulsed by said pulse generator means, converted to analog notation by said decorder and recorded upon activation of said flip-flop circuit means by said differentiator means.

3. A digitally controlled signal comparator as recited in claim 2 wherein said flip-flop circuit means is enabled by the pulse succeeding said selected pulse emitted by said BCD-to-decimal decoder during the period of a cycle determined by said decade counter.

4. A digitally controlled signal comparator as recited in claim 2 wherein said sampled and stored signal is continuously compared with all subsequent signals for the finite time period of pulses following the pulse enabling said flip-flop circuit means, said recorded pulses being limited by output of said differentiator circuit means which will maintain the preset activation of said flip-flop whereby only signals of predetermined value will be transmitted to said memory and recording means.

5. A digitally controlled signal comparator for selectively recording without interruption the physical characteristics of a fluid material being tested comprising:
   a. sampling and storing means receiving the raw input signal;
   b. memory and recording means connected to and receiving signals from said sampling and storing means;
   c. differentiator circuit means connected to said sampling and storing means and to said memory and recording means for selectively limiting voltages received by said memory and recording means;
   d. logic circuit means including interconnected repetitive pulse generating means, counter means, decoder means and flip-flop circuit means connected to said sampling and storing circuit means and said memory and recording circuit means whereby said raw input signal is selected, stored by said storing means for a period determined by the cycle of said decade counter pulsed by said pulse generator means, converted to analog notation by said decoder and recorded upon activation of said flip-flop circuit means by said differentiator means if said raw input signal is within said selected voltage limits of said differentiator.

* * * * *